United States Patent
Brace

(10) Patent No.: US 12,398,084 B2
(45) Date of Patent: Aug. 26, 2025

(54) DISTILLATION PROCESS AND APPARATUS WITH PRESSURE CORRECTED TEMPERATURE HEAT SOURCE CONTROL

(71) Applicant: Ineos Acetyls UK Limited, Lyndhurst (GB)

(72) Inventor: James William Brace, Camerton (GB)

(73) Assignee: Ineos Acetyls UK Limited, Lyndhurst (GB)

( * ) Notice: Subject to any disclaimer, the term of this patent is extended or adjusted under 35 U.S.C. 154(b) by 113 days.

(21) Appl. No.: 18/030,532

(22) PCT Filed: Sep. 30, 2021

(86) PCT No.: PCT/EP2021/077018
§ 371 (c)(1),
(2) Date: Apr. 6, 2023

(87) PCT Pub. No.: WO2022/073855
PCT Pub. Date: Apr. 14, 2022

(65) Prior Publication Data
US 2023/0416173 A1 Dec. 28, 2023

(30) Foreign Application Priority Data
Oct. 6, 2020 (GB) .................................. 2015833

(51) Int. Cl.
*C07C 7/04* (2006.01)
*B01D 3/42* (2006.01)
*C07C 51/44* (2006.01)

(52) U.S. Cl.
CPC .............. *C07C 7/04* (2013.01); *B01D 3/4211* (2013.01); *B01D 3/4294* (2013.01); *C07C 51/44* (2013.01)

(58) Field of Classification Search
CPC .......... B01D 3/4211; C07C 7/04; C07C 51/44
See application file for complete search history.

(56) References Cited

U.S. PATENT DOCUMENTS 3,238,111 A 3/1966 Harper
3,464,895 A 9/1969 Boyd
(Continued)

FOREIGN PATENT DOCUMENTS

EP 0849250 A1 6/1998
EP 0999198 A1 5/2000
(Continued)

OTHER PUBLICATIONS

Jones, J. H. "The Cativa Process for the Manufacture of Acetic Acid." Platinum Metals Rev., 2000, vol. 44, No. 3, pp. 94-105.
Howard, M. J. et al. "C1 to acetyls: catalysis and process." Catalysis Today, 1993, vol. 18, pp. 325-354.
Sunley, G. J. & Watson, D. J. "High productivity methanol carbonylation catalysis using iridium—The Cativa process for the manufacture of acetic acid." Catalysis Today, 2000, vol. 58, pp. 293-307.
(Continued)

*Primary Examiner* — Renee Robinson
(74) *Attorney, Agent, or Firm* — MCDONNELL BOEHNEN HULBERT & BERGHOFF LLP

(57) ABSTRACT

The present disclosure relates generally to processes and apparatuses for separating an effluent in an acetic acid production unit. Accordingly, one aspect of the disclosure provides a process including introducing a feed stream comprising acetic acid and water into a distillation column through a feed inlet, separating the feed stream to form a water-rich first fraction and an acetic acid-rich second fraction, measuring an internal temperature and an internal pressure of the column at positions between a first outlet and a second outlet of the column, determining a corrected temperature of the column based on the measured internal pressure and internal temperature of the column, adjusting a heating rate of a heat source in thermal communication with a bottom section of the column if the corrected temperature differs from a target value, and then withdrawing at least a portion of the separated acetic acid-rich second fraction, the fraction comprising 500-1,500 ppm water by weight (ppmw).

14 Claims, 1 Drawing Sheet

(56) References Cited

U.S. PATENT DOCUMENTS

| | | | |
|---|---|---|---|
| 4,578,151 | A | 3/1986 | Soderstrom, III et al. |
| 5,368,699 | A | 11/1994 | Rhiel et al. |
| 6,552,221 | B1 | 4/2003 | Hallinan et al. |
| 2013/0058842 | A1 | 3/2013 | Patt |
| 2017/0320804 | A1 | 11/2017 | Ligon et al. |
| 2018/0282253 | A1* | 10/2018 | Shimizu ................. B01D 3/009 |
| 2018/0354884 | A1 | 12/2018 | Shimizu et al. |
| 2019/0367439 | A1 | 12/2019 | Miura et al. |

FOREIGN PATENT DOCUMENTS

| | | |
|---|---|---|
| EP | 3401303 A1 | 11/2018 |
| JP | H03109902 A | 5/1991 |
| WO | 83/03825 A1 | 3/1983 |
| WO | 2008/144008 A1 | 11/2008 |

OTHER PUBLICATIONS

BP Acetic Acid (chemically pure) sales specification. Revision 10.0—Aug. 2009, 2 pages.

Yau, Te-Lin. "Zircadyne improves organic production." Outlook (Teledyne Wah Chang corporate newsletter/publication). 1995 Q1, vol. 16, No. 1, 2 pages.

Kister, H. Z. "Distillation Operation." McGraw-Hill 1990, pp. 560-563.

International Search Report and Written Opinion of International Application No. PCT/EP2021/077018, mailed Feb. 11, 2022, 15 pages.

Search Report of UK Patent Application No. GB2015833.3, mailed Mar. 19, 2021, 1 page.

\* cited by examiner

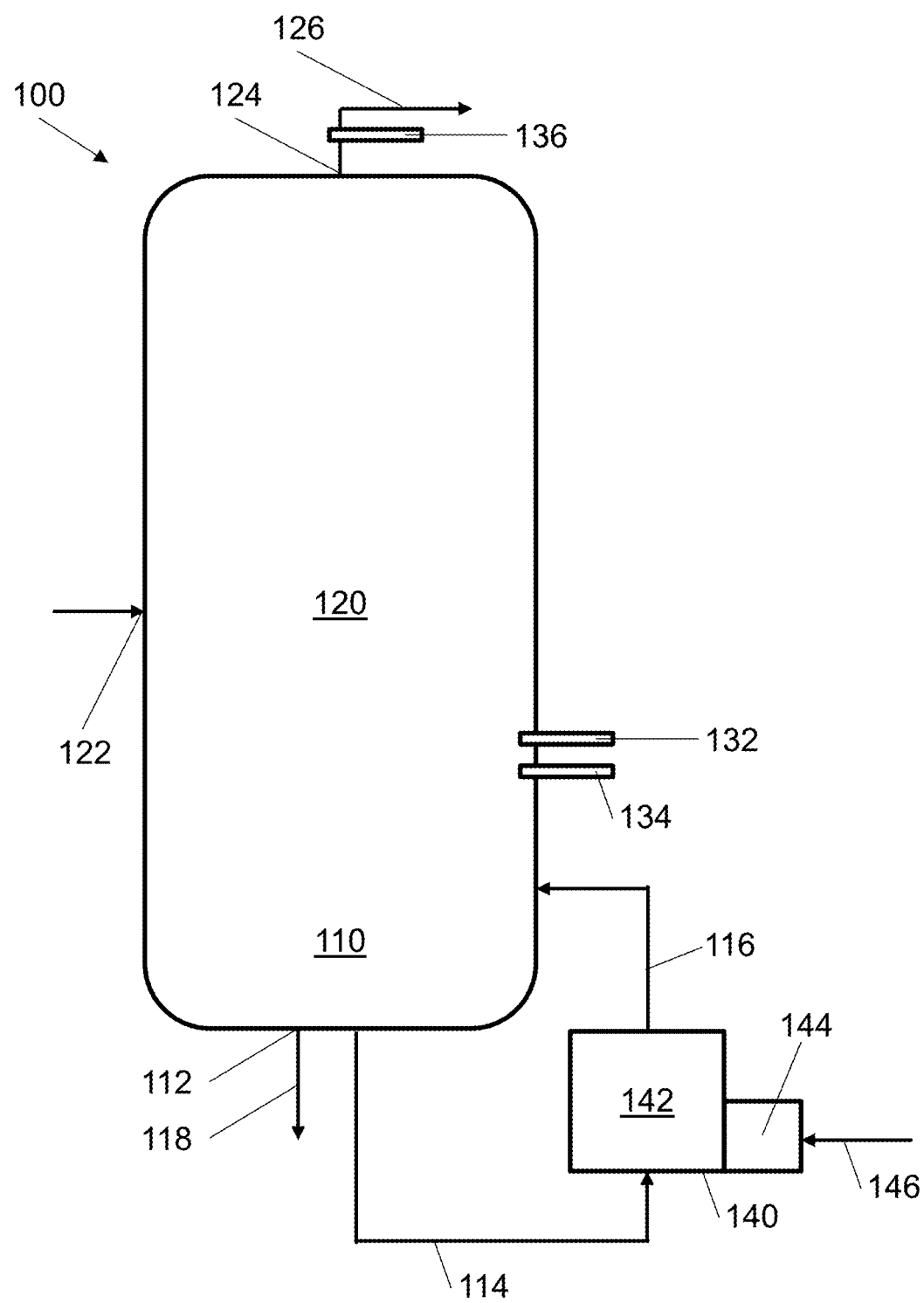

DISTILLATION PROCESS AND APPARATUS WITH PRESSURE CORRECTED TEMPERATURE HEAT SOURCE CONTROL

CROSS-REFERENCE TO RELATED APPLICATIONS

This application is a U.S. national phase application of International Patent Application No. PCT/EP2021/077018, filed Sep. 30, 2021, which claims the benefit of UK Provisional Patent Application no. 2015833.3, filed on Oct. 6, 2020, each of which is incorporated by reference in its entirety.

FIELD

The present disclosure relates generally to processes and apparatuses for separating an effluent in an acetic acid production unit.

TECHNICAL BACKGROUND

Acetic acid has been manufactured commercially for many years by carbonylating methanol with carbon monoxide in the presence of a Group VIII carbonylation catalyst. Typically, carbon monoxide is contacted with methanol in the presence of a rhodium or an iridium homogeneous or heterogeneous carbonylation catalyst, methyl iodide and water in a reactor. In general, acetic acid product may be recovered by withdrawing crude acetic acid product from the reactor and separating the acetic acid product in one or more flash and/or distillation stages from the other components, such as the Group VIII metal carbonylation catalyst, methyl iodide, methyl acetate, and water.

Conventionally, effluent from the reaction zone of an acetic acid production unit is separated in a flash separation zone, such as a flash tank, to provide a stream comprising acetic acid, "light" components such as methyl iodide and methyl acetate, and "heavy" components such as acetic anhydride and/or propionic acid. (As used herein "light components" refers to components having a boiling point lower than acetic acid and "heavy components" refers to components with a boiling point higher than acetic acid.) The stream is transferred to a light-ends separation zone, where light components including water are separated from acetic acid product in one or more distillation columns. Finally, heavy components are separated from acetic acid product in one or more "heavy-ends" columns (or heavy ends separation zone).

Because directly monitoring the composition of a product stream of a distillation column is difficult (e.g., due to costs, complexity, measurement dead-time), the composition of the product stream is often inferred from an internal temperature of the column. For example, the water content of the acetic acid stream from a light-ends distillation column may be inferred from a temperature measured at a particular location in the column. The amount of heat provided to the distillation column is then adjusted to maintain a "target" temperature (i.e., corresponding to a desired product composition).

However, the operating pressure of such columns is typically fixed/controlled at the top of the column or even downstream of a condenser of the column. The pressure drop within that column (i.e., from the fixed head pressure) can change, for example, when the vapour flow throughout the column increases or decreases. Changes in plant production rate can result in changes in vapour and liquid flows within the column and introduce significant changes in pressure drop. When the pressure at the temperature measurement point within the column changes, the same internal column temperature will no longer be indicative of a fixed product stream composition. In certain situations, the column pressure may be controlled even further downstream. For example, in the case of a light-ends column the pressure may be controlled at the outlet of a light-ends scrubbing system and the operating pressure of the light-ends column may actually be dictated by the established back pressure through intermediate equipment, which will vary according to operational adjustments. This introduces further challenges when attempting to determine a suitable temperature that is indicative of a desired product composition.

Accordingly, there remains a need to improve separation processes for streams comprising water and acetic acid, especially those resulting from the carbonylation of methanol.

SUMMARY

The scope of the present disclosure is not affected to any degree by the statements in this summary.

In one aspect, the disclosure provides a process for separating a feed stream comprising acetic acid and water in a distillation column, the column comprising
 a bottom section in thermal communication with a heat source;
 a feed inlet positioned above the bottom section;
 a first outlet positioned above the feed inlet; and
 a second outlet positioned below the feed inlet;
the process comprising
 introducing the feed stream into the column through the feed inlet;
 at a first heating rate of the heat source, separating the feed stream to form a water-rich first fraction and an acetic acid-rich second fraction;
 measuring an internal temperature of the column at a first position between the first outlet and the second outlet;
 measuring an internal pressure of the column at a second position between the first outlet and the second outlet;
 determining a corrected temperature of the column based on the measured internal pressure and internal temperature of the column; and
  determining that the corrected temperature is greater than a target value, and then adjusting the heat source to a second heating rate lower than the first heating rate; or
  determining that the corrected temperature is lower than a target value, and then adjusting the heat source to a second heating rate greater than the first heating rate;
 withdrawing at least a portion of the first fraction through the first outlet; and
 withdrawing at least a portion of the second fraction through the second outlet, wherein water is present in the withdrawn second fraction in an amount within the range of 500 ppm to 1,500 ppm by weight (ppmw).

In certain embodiments of the processes as otherwise described herein, water is present in the withdrawn second fraction in an amount within the range of 800 ppmw to 1,200 ppmw.

In certain embodiments of the processes as otherwise described herein, acetic acid is present in the withdrawn second fraction in an amount of at least 95 wt. % (e.g., at least 97.5 wt. %, or at least 99 wt. %).

In certain embodiments of the processes as otherwise described herein, the feed stream comprises 1-10 wt. % (e.g., 2-7.5 wt. %, or 2-5 wt. %) water, 90-99 wt. % (e.g., 92.5-98 wt. %, or 95-98 wt. %) acetic acid, up to 1 wt. % (e.g., up to 0.75 wt. %) methyl iodide, and up to 5 wt. % (e.g. up to 3.5 wt. %) methyl acetate. The feed stream may also comprise heavy components, such as acetic anhydride and/or propionic acid. There may be present, for example, 100-2,000 ppmw (e.g., 200-1,750 ppmw, or 400-1,500 ppmw) of acetic anhydride and/or propionic acid, such as 100-2,000 ppmw (e.g., 200-1,750 ppmw, or 400-1,500 ppmw) of propionic acid, In certain embodiments of the processes as otherwise described herein, the feed stream comprises 1-10 wt. % (e.g., 2-7.5 wt. %, or 2-5 wt. %) water, 40-85 wt. % (e.g., 40-75 wt. %, or 55-85 wt. %) acetic acid, 10-25 wt. % (e.g., 15-20 wt. %) methyl iodide, and 15-30 wt. % (e.g., 20-25 wt. %) methyl acetate. The feed stream may also comprise heavy components, such as acetic anhydride and propionic acid. There may be present, for example, 100-2,000 ppmw (e.g., 200-1,750 ppmw, or 400-1,500 ppmw) of acetic anhydride and/or propionic acid, such as 100-2,000 ppmw (e.g., 200-1,750 ppmw, or 400-1,500 ppmw) of propionic acid, In certain embodiments of the processes as otherwise described herein, the internal temperature and the internal pressure of the column are each individually measured at a position between the feed inlet and the second outlet.

In certain embodiments of the processes as otherwise described herein, the internal temperature and the internal pressure of the column are each individually measured at a position separated from the second outlet by no more than 50% (e.g., no more than 45%, or no more than 40%) of a total number of theoretical stages separating the first outlet and the second outlet.

In certain embodiments of the processes as otherwise described herein, the measured internal pressure is within the range of 0.125 MPaG to 0.5 MPaG.

In certain embodiments of the processes as otherwise described herein, the measured internal pressure is greater than a head pressure of the column (e.g., by at least 0.01 MPaG, or at least 0.02 MPaG, or at least 0.03 MPaG).

In certain embodiments of the processes as otherwise described herein, the measured internal temperature is within the range of 110° C. to 200° C. (e.g., within the range of 120° C. to 190° C., or 130° C. to 180° C.).

In certain embodiments of the processes as otherwise described herein, determining the corrected temperature comprises adding a correction factor to the measured internal temperature of the column, the correction factor based on the measured internal pressure of the column.

In certain embodiments of the processes as otherwise described herein, the heat source comprises a reboiler.

In certain embodiments of the processes as otherwise described herein, adjusting the heat source comprises increasing or decreasing the flowrate of steam provided to the reboiler.

In certain embodiments of the processes as otherwise described herein at least one of the bottom section, the second outlet, the internal surfaces of the heat source, any connecting pipework between the second outlet and the heat source, and any internals in the bottom section of the column comprise zirconium. (The term "internals" includes any components inside the column, and in the present invention includes, but is not limited to, trays and packing in the bottom section of the distillation column.)

In certain embodiments of the processes as otherwise described herein, the bottom section of the column and/or the second outlet comprise zirconium.

In certain embodiments of the processes as otherwise described herein, the second outlet comprises zirconium.

In certain embodiments of the processes as otherwise described herein, the withdrawn second fraction is separated to produce a product stream comprising acetic acid and water, and a waste stream comprising heavy components, such as acetic anhydride and/or propionic acid, and in particular a waste stream comprising propionic acid.

In particular, the second fraction may comprise acetic acid, water and heavy components, such as acetic anhydride and/or propionic acid, and the process may comprise also a step of passing all or a portion of the withdrawn second fraction to a second distillation column, and in particular a "heavy-ends column", to separate the heavy components. In preferred embodiments the second distillation column comprises a bottom section in thermal communication with a heat source;
a feed inlet ("second column feed inlet") positioned above the bottom section;
an outlet ("third outlet") positioned below the feed inlet; and
an outlet ("fourth outlet") positioned above the feed inlet;

the process comprising
introducing all or a portion of the second fraction into the column through the feed inlet;
withdrawing a heavy component-containing third fraction through the outlet positioned below the feed inlet and withdrawing an acetic acid-rich fourth fraction through the outlet positioned above the feed inlet.

In some embodiments the second distillation column may comprise two outlets positioned above the feed inlet, both of which have withdrawn therefrom acetic acid-rich fractions. One such fraction may be taken as the aforementioned fourth fraction, and preferably is taken as a product stream, whilst the other, preferably smaller flow rate fraction, may be taken as a recycle stream.

In another aspect, the disclosure provides a system for separating a feed stream comprising acetic acid and water, the system comprising a distillation column capable of separating the feed stream to produce a water-rich first stream and an acetic acid-rich second stream, the second stream comprising water in an amount within the range of 500 ppmw to 1,500 ppmw, the column comprising
a bottom section in thermal communication with a heat source;
a feed inlet positioned above the bottom section;
a first outlet positioned above the feed inlet;
a second outlet positioned below the feed inlet;
a temperature sensor positioned between the first outlet and the second outlet; and
a pressure sensor positioned between the first outlet and the second outlet;

the heat source comprising a reboiler and a control unit capable of adjusting a heating rate of the reboiler based on an internal temperature measurement of the temperature sensor and an internal pressure measurement of the of the pressure sensor.

In certain embodiments of the systems as otherwise described herein, the temperature sensor and the pressure sensor are each individually positioned between the feed inlet and the second outlet.

In certain embodiments of the systems as otherwise described herein, the temperature sensor and the pressure sensor are each individually separated from the second outlet by no more than 50% (e.g., no more than 45%, or no more than 40%) of a total number of theoretical stages separating the first outlet and the second outlet.

In certain embodiments as otherwise described herein, the system further comprises a head pressure sensor capable of measuring a head pressure of the column.

In certain embodiments of the systems as otherwise described herein at least one of the bottom section, the second outlet, the internal surfaces of the heat source, any connecting pipework between the second outlet and the heat source, and any internals in the bottom section of the column comprise zirconium.

In certain embodiments of the systems as otherwise described herein, the bottom section of the column and/or the second outlet comprise zirconium.

In certain embodiments of the systems as otherwise described herein, the second outlet comprises zirconium.

Other aspects of the disclosure will be apparent to those skilled in the art in view of the description that follows.

BRIEF DESCRIPTION OF THE DRAWINGS

FIGURE is a schematic view of a distillation system in accordance with one embodiment of the present disclosure.

DETAILED DESCRIPTION

In various aspects, the processes of the disclosure provide for improved separation of a feed stream comprising acetic acid and water.

Additional features of the processes of the disclosure will now be described in reference to the drawing FIGURE.

The present inventors have determined that by separating a feedstream comprising acetic acid and water in a distillation column, measuring an internal pressure and an internal temperature of the column, and then calculating a corrected internal temperature of the column, a heat source in thermal communication with a bottom section of the distillation column can be adjusted to maintain the corrected internal temperature at or near a target value.

Advantageously, the target value can correspond to the water concentration of an acetic acid-rich stream withdrawn from the column that desirably limits the corrosiveness of the system, and avoids unnecessary energy expenditure.

In particular, in the present invention the amount of water present in the withdrawn second fraction is maintained within the range of 500 ppmw to 1,500 ppmw. This range has been found to provide an optimum which minimizes or even avoids corrosion of certain materials (e.g. zirconium), whilst also minimizing unnecessary energy expenditure (e.g., reboiler duty). As already noted, preferably water is present in the withdrawn second fraction in an amount within the range of 800 ppmw to 1,200 ppmw.

Thus, whilst in general terms distillation columns for separating an impurity from a desired component are usually operated to minimize the impurity content of the obtained stream of the desired component, where the desired component is acetic acid and the impurity is water, as in the present invention, then it has been found that concentrations of water below 500 ppmw in the product stream can result in increased corrosion in the system.

In particular, mixtures of acetic acid and water are known to be corrosive under the conditions in the distillation column. For this reason at least the bottom section of the distillation column and the second outlet, but typically also ancillary equipment at the base of the column (such as the heat source (typically comprising one or more reboilers), base pumps, valves, pipework etc), may be fabricated or lined with materials which are resistant to corrosion. Zirconium is preferred. However, it has now been found that such materials still can corrode significantly if the water concentration in the product stream (and correspondingly therefore in bottom section of the column and at the second outlet) is too low.

Thus, in the present invention not only is it desired that the concentration of water is not too high, to avoid or minimize any subsequent steps for removing water for the acetic acid to meet product specification, but also it is desired that the concentration is not too low either, because this can cause corrosion issues. In order to maintain the concentration within such a range accurate control of the column is required. The present invention uses a corrected temperature, as defined, not to minimize the level of impurity, but to control it to be within the range required.

Accordingly, one aspect of the disclosure provides a process including introducing a feed stream comprising acetic acid and water into a distillation column through a feed inlet, separating the feed stream to form a water-rich first fraction and an acetic acid-rich second fraction, measuring an internal temperature and an internal pressure of the column at respective positions between a first outlet a second outlet of the column, determining a corrected temperature of the column based on the measured internal pressure and internal temperature of the column, adjusting a heating rate of a heat source in thermal communication with a bottom section of the column if the corrected temperature differs from a target value, and withdrawing at least a portion of the separated acetic acid-rich second fraction, the fraction comprising 500-1,500 ppm water by weight (ppmw). As used herein, unless further defined, a water-rich fraction has relatively more water than a corresponding acetic acid-rich fraction; while an acetic acid-rich fraction has relatively more acetic acid than a corresponding water-rich fraction.

As described above, the feed stream comprises acetic acid and water. In certain embodiments as otherwise described herein, the feed stream comprises a vapour fraction from a flash separation zone of an acetic acid production unit. In other embodiments as otherwise described herein, the feed stream comprises a fraction from a light-ends column in a light-ends separation zone of an acetic acid production unit. The feed stream may comprise any fraction from such a light-ends column which is enriched in acetic acid, such as a bottoms fraction from the light-ends column. As used herein, an "acetic acid production unit" comprises a unit capable of producing an acetic acid product. According to an embodiment of the disclosure, an acetic acid production unit includes a reaction zone, a flash separation zone, a light-ends separation zone, and a heavy-ends separation zone.

In certain embodiments, the reaction zone of the acetic acid production unit comprises any suitable reaction unit that can be used to produce an acetic acid-containing effluent. For example, in certain such embodiments, the reaction zone of the acetic acid production unit includes one or more reactors, within which acetic acid can be produced by carbonylation of methanol and/or a reactive derivative thereof with carbon monoxide in the presence of a Group VIII metal catalyst system. Suitable reactors which may be employed in the carbonylation of methanol and/or a reactive derivative thereof, and configuration thereof, are generally known in the art.

For example, in certain embodiments, the carbonylation of methanol and/or a reactive derivative thereof with carbon monoxide in the presence of a Group VIII metal carbonylation catalyst and methyl iodide is performed to produce acetic acid in the reaction zone of an acetic acid production unit. In certain embodiments, the reactive derivative of methanol is, for example, methyl acetate, dimethyl ether, or methyl iodide. Processes and Group VIII metal catalysts for the carbonylation of methanol are generally known in the art.

In certain embodiments, carbonylation of methanol and/or a reactive derivative thereof with carbon monoxide in the presence of a Group VIII metal catalyst system can be homogeneous or heterogeneous. For example, in certain embodiments, heterogeneous carbonylation is catalyzed by a Group VIII metal carbonylation catalyst (e.g., comprising rhodium and/or iridium) supported on an inert support (e.g., carbon, activated carbon). In certain such embodiments, the catalyst further comprises at least one metal promoter such as, for example, ruthenium, iron, nickel, lithium, and cobalt. In certain such embodiments, the methanol reactant can be provided to the reaction zone in the liquid and/or vapour phase. In certain desirable embodiments, methyl iodide and, optionally, water, are provided to the reaction zone in the vapour phase.

In another example, in certain embodiments, homogeneous carbonylation is catalyzed by a soluble Group VIII metal carbonylation catalyst (e.g., comprising rhodium and/or iridium) in a liquid reaction composition comprising methyl iodide, methyl acetate, and water. In certain such embodiments, the liquid reaction composition further comprises acetic anhydride and/or propionic acid by-product. In such embodiments, the carbonylation catalyst can be added to the liquid reaction composition in any form that can dissolve in the liquid reaction composition, or is convertible to a soluble form.

In certain embodiments as otherwise described herein, the iridium-containing carbonylation catalyst is selected from $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-$, $[Ir(CO)_2Br_2]^-$, $[Ir(CO)_2I_2]^-$, $[Ir(CH3)I_3(CO)_2]^-$, $Ir_4(CO)_{12}$, $IrCl_3 \cdot 4H_2O$, $IrBr_3 \cdot 4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. In certain desirable embodiments, the catalyst comprises a chloride-free complex of iridium such as, for example, acetates, oxalates, and acetoacetates. In certain embodiments as otherwise described herein, the concentration of iridium-containing carbonylation catalyst in the liquid reaction composition is within the range of 100 ppm to 6,000 ppm by weight (ppmw) of iridium.

In certain embodiments as otherwise described herein, the rhodium-containing carbonylation catalyst is selected from $[Rh(CO)_2Cl]_2$, $[Rh(CO)_2I]_2$, $[Rh(Cod)Cl]_2$, rhodium (III) chloride, rhodium (III) chloride trihydrate, rhodium (III) bromide, rhodium (III) iodide, rhodium (III) acetate, rhodium dicarbonylacetylacetonate, $RhCl_3(PPh_3)_3$ and $RhCl(CO)(PPh_3)_2$. In certain embodiments as otherwise described herein, the concentration of rhodium-containing carbonylation catalyst in the liquid reaction composition is at least 1 ppm (i.e., up to the solubility limit of the catalyst in the liquid reaction composition, or in a downstream separation zone), for example, within the range of 10 ppmw to 1,500 ppmw of rhodium.

In certain embodiments as otherwise described herein, the liquid reaction composition comprises an iridium carbonylation catalyst and further comprises a promoter selected from ruthenium, osmium, and rhenium. For example, in certain desirable embodiments, the liquid reaction composition comprises an iridium carbonylation catalyst and further comprises a ruthenium-containing compound soluble in the liquid reaction composition. In such embodiments, the ruthenium-containing compound can be added to the liquid reaction composition in any form that can dissolve in the liquid reaction composition, or is convertible to a soluble form. In certain such embodiments, the ruthenium-containing compound comprises a chloride-free compound such as, for example, acetates. In certain such embodiments, the ruthenium-containing compound is selected from ruthenium (III) chloride, ruthenium (III) chloride trihydrate, ruthenium (IV) chloride, ruthenium (III) bromide, ruthenium (III) iodide, ruthenium metal, ruthenium oxides, ruthenium (III) formate, $[Ru(CO)_3I_3]^-H^+$, tetra(aceto)chlororuthenium (II, III), ruthenium (III) acetate, ruthenium (III) propionate, ruthenium(III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium (II), tetrachlorobis(benzene)diruthenium(II), dichloro(cycloocta-1,5-diene)ruthenium (II) polymer and tris(acetylacetonate)ruthenium (III). In certain desirable embodiments, the ruthenium-containing compound is free of impurities that provide or can generate in-situ ionic iodides that can inhibit the reaction, such as, for example, alkali or alkaline earth metal salts, or other metal salts.

In certain embodiments, the ruthenium promoter is present in the liquid reaction composition in an effective amount (e.g., up to the solubility limit of the promoter in the liquid reaction composition, or in a downstream separation zone).

In other embodiments, the liquid composition comprises a rhodium carbonylation catalyst and further comprises a promoter selected from alkali metals and/or an organic iodide such as, for example, a quaternary ammonium iodide. In certain desirable embodiments, the liquid composition comprises a rhodium carbonylation catalyst and further comprises a lithium iodide promoter.

In certain embodiments as otherwise described herein, the liquid reaction composition comprises a rhodium carbonylation catalyst, and methyl acetate is present in the liquid reaction composition in an amount within the range of 0.1 wt. % to 70 wt. %. In other embodiments, the liquid reaction composition comprises an iridium carbonylation catalyst, and methyl acetate is present in the liquid reaction composition in an amount within the range of 1 wt. % to 70 wt. %. In certain desirable embodiments, methyl acetate is present in the liquid reaction composition in an amount within the range of 2 wt. % to 50 wt. %, e.g., 3 wt. % to 35 wt. %.

As described above, water is present in the liquid reaction composition. The person of ordinary skill in the art will appreciate that water is formed in situ in the liquid reaction composition by the esterification reaction between methanol and acetic acid product. In certain embodiments, water may also be introduced to the carbonylation reaction zone (e.g., together with, or separately from other components of the liquid reaction composition). In certain desirable embodiments, water is present in the liquid reaction composition in an amount within the range of 0.1 wt. % to 15 wt. %, e.g., within the range of 1 wt. % to 15 wt. %, or within the range of 1 wt. % to 8 wt. %.

As described above, heavy components, such as propionic acid by-product, can also be present in the liquid reaction composition. In certain embodiments, propionic acid is present in the liquid reaction composition in an amount within the range of 200 ppmw to 2,500 ppmw, e.g., within the range of 400 ppmw to 2,000 ppmw, or within the range of 600 ppmw to 1,400 ppmw.

In certain desirable embodiments, methyl iodide is present in the liquid reaction composition in an amount within the range of 1 wt. % to 20 wt. %. For example, in certain such embodiments, methyl iodide is present in the liquid reaction composition in an amount within the range of 2 wt. % to 16 wt. %. In certain embodiments as otherwise described herein, the liquid reaction composition comprises a solvent. For example, in certain such embodiments, the liquid reaction composition comprises an acetic acid solvent (e.g., recycled from a separation zone of the acetic acid production unit).

As described above, acetic acid can be produced in the reaction zone by carbonylation of methanol and/or a reactive derivative thereof with carbon monoxide. In certain embodiments as otherwise described herein, the carbon monoxide provided to the reaction zone is essentially pure. In other embodiments, the carbon monoxide provided to the reaction zone contains one or more impurities such as, for example, carbon dioxide, methane, nitrogen, hydrogen, or noble gases. In certain embodiments as otherwise described herein, the partial pressure of carbon monoxide (e.g., in a reactor of the reaction zone) is within the range of 1 bar to 70 bar, e.g., within the range of 1 bar to 35 bar.

In certain embodiments as otherwise described herein, the carbonylation reaction is conducted at a total pressure (e.g., in a reactor of the reaction zone) within the range of 10 barg to 100 barg. In certain embodiments as otherwise described herein, the carbonylation reaction is conducted at a temperature (e.g., in a reactor of the reaction zone) within the range of 100° C. to 300° C. For example, in certain such embodiments, the carbonylation reaction is conducted at a temperature within the range of 150° C. to 210° C., or 170° C. to 195° C., or 185° C. to 195° C.

The carbonylation process can be conducted as a batch process or as a continuous process. In certain desirable embodiments, the carbonylation process is conducted as a continuous process.

As described above, the acetic acid production unit includes a flash separation zone configured to separate a crude acetic acid product from an effluent of the reaction zone. In certain embodiments as otherwise described herein, the flash separation zone comprises a tank for separating the effluent to form a liquid fraction (e.g., comprising carbonylation catalyst) and a vapour fraction comprising acetic acid and water. The vapour fraction withdrawn from the flash separation zone is transferred to a light-ends separation zone of the acetic acid production unit. In certain such embodiments, the liquid withdrawn from the tank is transferred to the reaction zone of the acetic production unit as recycle.

The light-ends separation zone of the acetic acid production unit is configured to separate at least the components of the vapour fraction that are more volatile than acetic acid from acetic acid. For example, in certain embodiments, acetic acid is produced in the reaction zone by carbonylation of methanol and/or a reactive derivative thereof with carbon monoxide in the presence of a Group VIII metal catalyst system, and the light-ends separation zone of the acetic acid production unit is configured to separate acetic acid and to further separate methyl iodide, methyl acetate and water, which can be recycled to the reaction zone.

The distillation column in the process of the present invention may be located in the light-ends separation zone of an acetic acid production unit. In certain embodiments, the light-ends separation zone comprises a distillation column that separates a crude acetic acid product comprising acetic acid and heavy components, such as propionic acid, from a light-ends fraction including methyl iodide, methyl acetate and water. In some embodiments this distillation column can produce a "dry" crude acetic acid stream. As used herein, a "dry" or "dried" acetic acid stream comprises water in an amount of at most 1,500 ppmw. In such embodiments this distillation column may be the distillation column in the process of the invention. (And in such embodiments it may also be considered as a combined light-ends and drying column.) In other embodiments, the light-ends separation zone comprises a first distillation column and a separate drying column. For example, the light-ends separation zone may include a first distillation column which separates a crude acetic acid stream (comprising acetic acid, heavy components and residual water) from methyl acetate and methyl iodide, and a separate drying column which separates residual water from the crude acetic acid stream to produce a "dry" crude acetic acid stream. In these embodiments the drying column may be the distillation column in the process of the invention. In either embodiment the dry crude acetic acid product comprises, in addition to acetic acid, heavy components, such as propionic acid. The dry crude acetic acid stream in either embodiment may then be passed to a heavy ends separation zone as described herein for separation of heavy components.

The FIGURE is a schematic cross-sectional view of a column in accordance with one embodiment of the present disclosure. As shown in the FIGURE, column 100 includes a bottom section 110 in thermal communication with a heat source 140 (i.e., providing heat to the bottom section at a heating rate), and above the bottom section 110, a fractionation section 120. In the embodiment of the FIGURE, the heat source 140 includes a reboiler 142 in fluid communication (through lines 114 and 116) with the bottom section 110 and a control unit 144 capable of adjusting a heating rate of the reboiler 142. In the embodiment of the FIGURE, the control unit 144 is capable of adjusting an amount of steam supplied to the reboiler 142 from a steam source 146.

Accordingly, in certain embodiments as otherwise described herein, the heat source is a reboiler, and adjusting the heat source (i.e., to provide heat to the bottom section at an increased or decreased heating rate) comprises adjusting an amount of steam supplied to the reboiler. Of course, in other embodiments, other heat-transfer mediums known in the art (e.g., hot oil, flue gases, process streams) can be supplied to the reboiler.

The column 100 includes a feed inlet 122 positioned above the bottom section 110, a first outlet 124 positioned above the feed inlet 122, and a second outlet 112 positioned below the feed inlet 122. In certain embodiments, the feed inlet is separated from a base of the column by 30-70% of the total number of theoretical stages present in the column. In certain embodiments, the first outlet is separated from the base of the column by at least 70% (e.g., at least 80%, or at least 90%) of the total number of theoretical stages present in the column. For example, in certain such embodiments, the first outlet is positioned at or near the top of the column. In certain embodiments, the second outlet is separated from a base of the column by no more than 30% (e.g., no more than 20%, or no more than 10%) of the total number of theoretical stages present in the column. For example, in certain such embodiments, the second outlet is positioned at or near the bottom of the column.

As described above, the column includes the fractionation section 120 including one or more fractionation trays (not shown). In certain embodiments as otherwise described herein, the fractionation section includes at least 10 trays, e.g., 10-100 trays, or 10-80 trays, or 25-100 trays, or 25-80 trays, or 40-100 trays, or 40-80 trays. In certain embodiments as otherwise described herein, the fractionation section includes at least 10 theoretical stages, e.g., 10-60 theoretical stages, or 15-60 theoretical stages, or 20-60 theoretical stages, or 10-50 theoretical stages, or 15-50 theoretical stages, or 20-50 theoretical stages, or 20-60 theoretical stages, or 20-50 theoretical stages, or 20-40 theoretical stages. In certain embodiments as otherwise described herein, the fractionation section contains one or more packed beds.

The column 100 includes a temperature sensor 132 positioned between the first outlet 124 and the second outlet 112, and a pressure sensor 134 positioned between the first outlet 124 and the second outlet 112. In certain embodiments as otherwise described herein, the temperature sensor is separated from the pressure sensor by no more than 10% (e.g., no more than 5%, or no more than 2.5%) of the total number of theoretical stages present in the column. In certain embodiments as otherwise described herein, both of the temperature sensor and the pressure sensor are positioned between two adjacent trays of the fractionation section. For example, in the embodiment of the FIGURE, the temperature sensor and the pressure sensor are positioned between a control tray and an adjacent tray. In the embodiment of the FIGURE, the temperature sensor 132 is positioned above the pressure sensor 134. Of course, in other embodiments, the temperature sensor and pressure sensor are positioned at similar distances from a base of the column, or the pressure sensor is positioned above the temperature sensor. Suitable temperature and pressure sensors (i.e., capable of determining, respectively, an internal temperature and an internal pressure of the column) are generally known in the art. The person of ordinary skill in the art will appreciate that the internal pressure of the column may not necessarily be measured directly and could be measured by calculation based on other suitable pressure measurements. For example, the internal pressure of the column at the second position could be measured by combining a measurement of column head pressure with a differential pressure measurement across a suitable section of the column to provide a measurement of the internal pressure of the column at the second position.

In the embodiment of the FIGURE, the temperature sensor and the pressure sensor are each positioned between the feed inlet 122 and the second outlet 112. In certain embodiments as otherwise described herein, the temperature sensor and the pressure sensor are each individually separated from a base of the column by no more than 50% (e.g., no more than 45%, or no more than 40%) of the total number of theoretical stages separating the first outlet and the second outlet.

The column 100 may include a head pressure sensor 136. In certain embodiments, the head pressure sensor is separated from a base of the column by at least 70% (e.g., at least 80%, or at least 90%) of the total number of theoretical stages present in the column. For example, in certain such embodiments, the head pressure sensor is positioned at or near the top of the column. In other embodiments, the head pressure sensor is positioned downstream of the first outlet of the column. For example, in the embodiment of the FIGURE, the head pressure sensor 136 is positioned downstream of the first outlet 124 (i.e., configured to measure the pressure of stream 126). Suitable pressure sensors for measuring a head pressure of the column, and configurations thereof, are generally known in the art.

In certain embodiments as otherwise described herein, one or more components of the column comprise zirconium. In certain embodiments as otherwise described herein, one or more (e.g., each) of the second outlet, bottom section, the reboiler, any connecting pipework between the second outlet and the heat source, and any internals in the bottom section of the column comprise zirconium. For example, in certain embodiments, the second outlet comprises zirconium.

In operation, a feed stream is introduced into the column 100 through the feed inlet 122. In certain embodiments as otherwise described herein, the pressure at the inlet is at least about 0.1 MPaG, e.g., within the range of 0.1 MPaG to 1 MPaG, or 0.1 MPaG to 0.5 MPaG. In certain embodiments as otherwise described herein, the feed stream comprises at least a portion of a vapour fraction withdrawn from a flash separation zone of an acetic acid production unit. In other embodiments, the feed stream comprises at least a portion of an effluent of a light-ends column (e.g., a distillation column which separates a crude acetic acid stream (comprising acetic acid, heavy components and residual water) from methyl acetate and methyl iodide).

The feed stream comprises water and acetic acid. In certain embodiments as otherwise described herein, the feed stream comprises at least 90 wt. % acetic acid. For example, in certain such embodiments, the feed stream comprises 90-99 wt. %, or 92.5-98 wt. %, or 95-98 wt. % acetic acid. In certain embodiments as otherwise described herein, the feed stream comprises 40-85 wt. % acetic acid. For example, in certain such embodiments, the feed stream comprises 40-75 wt. %, or 55-85 wt. % acetic acid. In certain embodiments as otherwise described herein, the feed stream comprises no more than 10 wt. % water. For example, in certain such embodiments, the feed stream comprises 1-10 wt. %, or 2-7.5 wt. %, or 2-5 wt. % water.

In certain embodiments as otherwise described herein, the feed stream further comprises heavy components, such as propionic acid. For example, in certain such embodiments, the feed stream comprises 100-2,000 ppmw (e.g., 200-1,750 ppmw, or 400-1,500 ppmw) heavy components, such as propionic acid and/or acetic anhydride. In certain such embodiments, the feed stream comprises 100-2,000 ppmw (e.g., 200-1,750 ppmw, or 400-1,500 ppmw) propionic acid. In certain embodiments, the feed stream further comprises one or more of methanol, methyl acetate, methyl iodide, carbon monoxide, carbon dioxide, inert gases (e.g., nitrogen), and other reaction by-product gases (e.g., hydrogen, methane). For example, in certain such embodiments, the feed stream comprises up to 1 wt. % methyl iodide (e.g., up to 0.75 wt. %, or up to 0.5 wt. % methyl iodide) and up to 5 wt. % methyl acetate (e.g., up to 3.5 wt. %, or up to 2 wt. % methyl acetate). In another example, in certain such embodiments, the feed stream comprises 10-25 wt. % methyl iodide (e.g., 15-20 wt. % methyl iodide) and 15-30 wt. % methyl acetate (e.g., 20-25 wt. % methyl acetate).

At a first heating rate of the reboiler 142 of the heat source 140, the feed stream separates to form a water-rich first fraction and an acetic acid-rich second fraction. An internal temperature of the column 100 is measured by the temperature sensor 132 (i.e., at a first position corresponding to the position of the temperature sensor 132 as otherwise described herein), and an internal pressure of the column is measured by the pressure sensor 134 (i.e., at a second position corresponding to the position of the pressure sensor 134 as otherwise described herein). In certain embodiments, the internal temperature and the internal pressure of the column are each individually measured at a position between the feed inlet and the second outlet. For example, in certain such embodiments, the internal temperature and the internal pressure of the column are each individually measured at a position separated from the second outlet by no more than 50% (e.g., no more than 45%, or no more than 40%) of the total number of theoretical stages separating the first outlet and the second outlet.

In certain embodiments as otherwise described herein, the measured internal pressure of the column is within the range of 0.125 MPaG to 0.5 MPaG. In certain embodiments, the measured internal pressure is greater than a head pressure of the column (e.g., measured by a head pressure sensor as otherwise described herein). For example, in certain such embodiments, the measured internal pressure is at least 0.01 MPaG, or at least 0.02 MPaG, or at least 0.03 MPaG greater than a head pressure of the column. In certain embodiments as otherwise described herein, the measured internal temperature of the column is within the range of 110° C. to 200° C. For example, in certain such embodiments, the measured internal temperature of the column is within the range of 120° C. to 190° C., or 130° C. to 180° C.

Based on the measured internal pressure and internal temperature of the column, a corrected temperature of the column is determined. In certain embodiments as otherwise described herein, determining the corrected temperature comprises adding a correction factor to the measured internal temperature of the column:

$$T_c = T_m - F(P_m)$$

where $T_c$ is the corrected temperature, $T_m$ is the measured internal temperature of the column, and $F(P_m)$ is the correction factor based on the measured internal pressure of the column $P_m$. In certain such embodiments, the correction factor is the solution to a linear equation:

$$F(P_m) = x * P_m + y$$

where x and y are real-number coefficients. The person of ordinary skill in the art can determine appropriate real-number coefficients, based, for example, on measured product compositions at one or more sets of distillation conditions. An example is provided in the Examples, below.

Advantageously, the present inventors have determined that the corrected temperature as otherwise described herein can be strongly correlated to the concentration of water present in the separated acetic acid-rich second fraction, and accordingly can more reliably indicate a deviation of distillation conditions away from those necessary to maintain desirable product compositions.

Accordingly, in certain embodiments as otherwise described herein, the determined corrected temperature is greater than a target value, and the heat source is adjusted to a second heating rate lower than the first heating rate. In other embodiments, the determined corrected temperature is less than a target value, and the heat source is adjusted to a second heating rate greater than the first heating rate. In the embodiment of the FIGURE, adjusting the heat source 140 of column 100 comprises using control unit 144 to increase or decrease an amount of steam provided to the reboiler 142 from the steam source 146.

At least a portion of the second fraction is withdrawn as stream 118 from the column 100 through the second outlet 112. As described above, the process as otherwise described herein can be maintained to produce a withdrawn second fraction having a desirable composition. The present inventors have further determined that an amount of water present in the withdrawn second fraction can be maintained within the range of 500 ppmw to 1,500 ppmw, which desirably minimizes or even avoids corrosion of certain materials (e.g., zirconium), as well as unnecessary energy expenditure (e.g., reboiler duty).

Accordingly, the second fraction withdrawn through the second outlet 112 comprises water in an amount within the range of 500 ppmw to 1,500 ppmw. In certain embodiments as otherwise described herein, water is present in the withdrawn second fraction in an amount within the range of 800 ppmw to 1,200 ppm. In certain embodiments as otherwise described herein, acetic acid is present in the withdrawn second fraction in an amount that is at least 95 wt. % (e.g., at least 97.5 wt. %, or at least 99 wt. %). In certain embodiments as otherwise described herein, the withdrawn second fraction further comprises 100-2,500 ppmw (e.g., 200-2,000 ppmw, or 600-1,500 ppmw) heavy components, such as propionic acid and/or acetic anhydride, such as comprises 100-2,500 ppmw (e.g., 200-2,000 ppmw, or 600-1,500 ppmw) propionic acid.

At least a portion of the first fraction is withdrawn as stream 126 from the column 100 through the first outlet 124. In certain embodiments, the withdrawn first fraction comprises water, acetic acid, and one or more of methanol, methyl acetate, methyl iodide, carbon monoxide, carbon dioxide, inert gases (e.g., nitrogen), and other reaction by-product gases (e.g., hydrogen, methane). In certain embodiments as otherwise described herein, the first fraction comprises 5-95 wt. % (e.g., 30-50 wt. %, or 70-90 wt. %) water, 5-50 wt. % (e.g., 5-20 wt. %, or 10-30 wt. %) acetic acid, and up to 70 wt. % (e.g., up to 20 wt. %, or 40-60 wt. %) of a combined amount of one or more of methanol, methyl acetate, methyl iodide, carbon monoxide, and carbon dioxide. For example, in certain embodiments, the first fraction comprises 70-90 wt. % water, 10-30 wt. % acetic acid, and up to 20 wt. % of a combined amount of one or more of methanol, methyl acetate, methyl iodide, carbon monoxide, and carbon dioxide. In another example, in certain embodiments, the first fraction comprises 30-50 wt. % water, 5-20 wt. % acetic acid, and 40-60 wt. % of a combined amount of one or more of methanol, methyl acetate, methyl iodide, carbon monoxide, and carbon dioxide.

In certain embodiments as otherwise described herein, the process further comprises one or more condensers and/or coolers to condense the withdrawn first fraction and form a liquid fraction. The person of ordinary skill in the art will appreciate that any suitable method known in the art to condense the withdrawn first fraction to the liquid phase can be employed. For example, in certain embodiments, the fraction is condensed using at least one heat exchanger (e.g., supplied with water as cooling medium). Components of the overhead fraction that are not condensed (e.g., carbon monoxide, carbon dioxide, inert gases, reaction by-product gases) are removed as an off-gas stream. In certain embodiments, acetic acid is produced in the reaction zone by carbonylation of methanol and/or a reactive derivative thereof with carbon monoxide in the presence of a Group VIII metal catalyst system, and the off-gas stream further comprises methyl iodide (e.g., present as entrained and/or evaporated methyl iodide), methyl acetate, and water.

In certain embodiments, the withdrawn first fraction comprises methyl acetate, water, and acetic acid. In certain embodiments, acetic acid is produced in the reaction zone by carbonylation of methanol and/or a reactive derivative thereof with carbon monoxide in the presence of a Group VIII metal catalyst system, and the withdrawn first fraction further comprises methyl iodide. In certain embodiments, the withdrawn first fraction further comprises entrained or dissolved gaseous components (e.g., carbon monoxide, carbon dioxide, inert gases).

In certain embodiments a portion of the withdrawn first fraction is condensed and returned to a distillation column, and preferably to the distillation column from which the first fraction is withdrawn, as a reflux stream. In certain embodiments the process comprises a decanter, in which the withdrawn first fraction is separated into two layers: a lower (e.g., organic) layer comprising methyl acetate and methyl iodide and an upper (e.g., aqueous) layer comprising water. In certain embodiments, acetic acid is produced in the reaction zone by carbonylation of methanol and/or a reactive derivative thereof with carbon monoxide in the presence of a Group VIII metal catalyst system, and the lower layer further comprises methyl iodide. In certain embodiments, at least a portion (e.g., all) of the upper layer from the decanter is returned to a distillation column, and preferably to the distillation column from which the first fraction is withdrawn, as a reflux stream. In certain embodiments, at least a portion (e.g., all) of the upper layer from the decanter is recycled to the reaction zone. In certain embodiments, off-gas is withdrawn from the decanter and transferred to an off-gas scrubbing unit (e.g., before disposal).

In certain embodiments, at least a portion of the withdrawn second fraction including acetic acid and heavy components, such as propionic acid and/or acetic anhydride, is transferred to a heavy-ends column through a feed inlet positioned at an intermediate point in the column. In such embodiments, a waste stream comprising heavy components such as propionic acid and/or acetic anhydride is withdrawn from the heavy-ends column through a heavy product outlet, and acetic acid is removed as a product stream at one or more outlets of the column (e.g., as an overhead stream from an outlet at the top of the column, as a sidedraw stream from an outlet positioned higher than the feed inlet). In certain embodiments, the product stream comprises essentially acetic acid. In certain embodiments, the product stream comprises essentially acetic acid, and comprises less than 1,500 ppmw of water. In certain desirable embodiments, the product stream comprises essentially acetic acid, and comprises less than 1,500 ppmw of a combined total of acetic anhydride, propionic acid and water. Suitable columns which may be employed as a heavy-ends column, and configurations thereof, are generally known in the art. For example, in certain embodiments, the heavy-ends column is connected to a condenser. In another example, in certain embodiments, a reboiler is connected to the base of the heavy-ends column.

EXAMPLES

The Examples that follow are illustrative of specific embodiments of the invention, and various uses thereof. They are set forth for explanatory purposes only, and are not to be taken as limiting the invention.

Example 1. Combined Light-Ends and Drying Column

A reboiled, combined light-ends and drying column of a light-ends separation zone was modeled with ASPEN Plus (Aspen Technology Inc., Bedford, MA). The tray column included 28 theoretical stages between a first outlet at the top of the column and a second outlet at the base of the column. An internal pressure and an internal temperature of the column were measured between two adjacent trays, at a position separated from the second outlet by about 6 theoretical stages, and then used to calculate a corrected temperature of the column, according to Formula I:

$$T_c = T_m - (142.35 * P_m - 24.951)$$

where $T_c$ is the corrected temperature (in °C.), $T_m$ is the measured internal temperature (in °C.), and $P_m$ is the measured internal temperature (in MPaG).

In a baseline run B, the head pressure of the column was 0.1297 MPaG, and the pressure at the base of the column was 0.1867 MPaG, providing an average pressure drop across the column of approximately 20 mbar/theoretical stage. At a measured internal temperature and internal pressure of the column of 146.49° C. and 0.1751 MPaG, respectively, the water concentration of an acetic acid-rich stream withdrawn from the second outlet was 1,000 ppmw. Accordingly, the target value corresponding to 1,000 ppmw water was 146.5° C.

In a run E1, the average pressure drop across the column was increased to 24 mbar/theoretical stage to simulate a change in feed stream throughput to the distillation column. The head pressure of the column remained at 0.1297 MPaG, but the pressure at the base of the column increased to 0.1981 MPaG. The measured internal pressure increased to 0.1848 MPaG. To maintain the corrected internal temperature at the target value of 146.5° C., the amount of steam supplied to the column reboiler was adjusted to increase the heating rate of the reboiler, which increased the measured internal temperature of the column to 147.85° C., as shown in Table 1, below. By controlling the steam supply to the column reboiler to maintain the desired corrected temperature, the water concentration of an acetic acid-rich stream withdrawn from the second outlet decreased only to 970 ppmw.

In a comparative run C1, the above pressure change was again simulated, but the steam supply to the column reboiler was controlled only to maintain the measured internal temperature at 146.49° C. As shown in Table 1, below, the resulting water concentration of the acetic acid-rich stream increased to 1,620 ppmw, significantly greater than generally acceptable levels for commercial applications.

In a run E2, the average pressure drop across the column was decreased to 12 mbar/theoretical stage to simulate a change in feed stream throughput to the distillation column. The head pressure of the column remained at 0.1297 MPaG, but the measured internal pressure decreased to 0.1572 MPaG. To maintain the corrected internal temperature at the target value of 146.5° C., the amount of steam supplied to the reboiler was adjusted to decrease the heating rate of the reboiler, which decreased the measured internal temperature of the column to 143.93° C., as shown in Table 1, below. By controlling the steam supply to the column reboiler to maintain the desired corrected temperature, the water concentration of an acetic acid-rich stream withdrawn from the second outlet increased only to 1040 ppmw.

In a comparative run C2, the above pressure change was again simulated, but the steam supply to the column reboiler was controlled only to maintain the measured internal temperature at 146.49° C. As shown in Table 1, below, the resulting water concentration of the acetic acid-rich stream decreased to 410 ppmw. At such concentrations, the stream could corrode distillation equipment including the second outlet, reboiler and bottom section. Moreover, because water concentrations greater than 410 ppmw are acceptable in commercial applications, more energy was expended to drive distillation than was necessary.

TABLE 1

| | | Distillation Runs | | |
|---|---|---|---|---|
| Run | $P_m$ (MPaG) | $T_m$ (° C.) | $T_c$ (° C.) | water conc. (ppmw) |
| B | 0.1751 | 146.49 | 146.5 | 1,000 |
| E1 | 0.1848 | 147.85 | 146.5 | 970 |
| C1 | 0.1848 | 146.49 | — | 1,620 |
| E2 | 0.1572 | 143.93 | 146.5 | 1,040 |
| C2 | 0.1572 | 146.49 | — | 410 |

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for separating a feed stream comprising acetic acid and water in a distillation column, the column comprising
a bottom section in thermal communication with a heat source, the heat source having internal surfaces;
a feed inlet positioned above the bottom section;
a first outlet positioned above the feed inlet; and
a second outlet positioned below the feed inlet;
the process comprising
introducing the feed stream into the column through the feed inlet;
at a first heating rate of the heat source, separating the feed stream to form a water-rich first fraction and an acetic acid-rich second fraction;
measuring an internal temperature of the column at a first position between the first outlet and the second outlet;
measuring an internal pressure of the column at a second position between the first outlet and the second outlet;
determining a corrected temperature of the column based on the measured internal pressure and internal temperature of the column; and
determining that the corrected temperature is greater than a target value, and then adjusting the heat source to a second heating rate lower than the first heating rate; or
determining that the corrected temperature is lower than a target value, and then adjusting the heat source to a second heating rate greater than the first heating rate;
withdrawing at least a portion of the first fraction through the first outlet; and
withdrawing at least a portion of the second fraction through the second outlet, wherein water is present in the withdrawn second fraction in an amount within the range of 500 ppm to 1500 ppm by weight (ppmw),
wherein at least one of the bottom section, the second outlet, the internal surfaces of the heat source, any connecting pipework between the second outlet and the heat source, and any internals in the bottom section of the column comprise zirconium.

2. The process of claim 1, wherein water is present in the withdrawn second fraction in an amount within the range of 800 ppmw to 1,200 ppmw.

3. The process of claim 1, wherein acetic acid is present in the withdrawn second fraction in an amount of at least 95 wt. %.

4. The process of claim 1, wherein the feed stream comprises 1-10 wt. % water, 90-99 wt. % acetic acid, up to 1 wt. % methyl iodide, and up to 5 wt. % methyl acetate.

5. The process of claim 1, wherein the feed stream comprises 1-10 wt. % water, 40-85 wt. % acetic acid, 10-25 wt. % methyl iodide, and 15-30 wt. % methyl acetate.

6. The process of claim 1, wherein the internal temperature and the internal pressure of the column are each individually measured at a position between the feed inlet and the second outlet.

7. The process of claim 1, wherein the internal temperature and the internal pressure of the column are each individually measured at a position separated from the second outlet by no more than 50% of a total number of theoretical stages separating the first outlet and the second outlet.

8. The process of claim 1, wherein the measured internal pressure is within the range of 0.125 MPaG to 0.5 MPaG.

9. The process of claim 1, wherein the measured internal temperature is within the range of 110° C. to 200° C.

10. The process of claim 1, wherein determining the corrected temperature comprises adding a correction factor to the measured internal temperature of the column, the correction factor based on the measured internal pressure of the column.

11. The process of claim 1, wherein the heat source comprises a reboiler.

12. The process of claim 1, wherein at least the bottom section and the second outlet comprise zirconium.

13. The process of claim 1, wherein the second outlet comprises zirconium.

14. The process of claim 1, further comprising separating the withdrawn second fraction to produce a product stream comprising acetic acid and water, and a waste stream comprising heavy components.

* * * * *